United States Patent [19]
Schaer

[11] Patent Number: 6,002,956
[45] Date of Patent: Dec. 14, 1999

[54] METHOD OF TREATING USING AN OVER-THE-WIRE EP CATHETER

[75] Inventor: Alan K. Schaer, Cupertino, Calif.

[73] Assignee: Cardima, Inc., Fremont, Calif.

[21] Appl. No.: 08/944,896

[22] Filed: Oct. 6, 1997

Related U.S. Application Data

[60] Continuation of application No. 08/473,525, Jun. 7, 1995, abandoned, which is a division of application No. 08/447,351, May 23, 1995, Pat. No. 5,782,760.

[51] Int. Cl.⁶ .......................... A61B 5/042; A61B 17/39
[52] U.S. Cl. .......................... 600/381; 606/41; 607/122
[58] Field of Search .................. 600/381, 374; 606/41; 607/98, 99, 115, 122

[56] References Cited

U.S. PATENT DOCUMENTS

| | | | |
|---|---|---|---|
| 4,519,403 | 5/1985 | Dickhudt | 128/785 |
| 4,832,048 | 5/1989 | Cohen | 128/642 |
| 5,184,621 | 2/1993 | Vogel et al. | 128/642 |
| 5,257,635 | 11/1993 | Langberg | 606/41 |
| 5,334,193 | 8/1994 | Nardella | 606/41 |
| 5,423,811 | 6/1995 | Imran et al. | 607/122 |
| 5,500,012 | 3/1996 | Brucker et al. | 607/122 |
| 5,509,411 | 4/1996 | Littmann et al. | 128/642 |
| 5,517,989 | 5/1996 | Frisbie et al. | 128/642 |
| 5,545,161 | 8/1996 | Imran et al. | 606/41 |
| 5,549,109 | 8/1996 | Samson et al. | 128/642 |
| 5,575,810 | 11/1996 | Swanson et al. | 607/99 |
| 5,645,064 | 7/1997 | Littmann et al. | 128/642 |

FOREIGN PATENT DOCUMENTS

| | | |
|---|---|---|
| 2032883 | 6/1991 | Canada . |
| 0 499 491 A3 | 8/1992 | European Pat. Off. . |
| 0 573 311 A1 | 12/1993 | European Pat. Off. . |
| 0 608 609 A2 | 8/1994 | European Pat. Off. . |
| 0 609 182 A1 | 8/1994 | European Pat. Off. . |
| 1690786 | 11/1991 | U.S.S.R. . |
| WO 94/02077 | 3/1994 | WIPO . |
| WO 94/16618 | 8/1994 | WIPO . |
| WO 94/16619 | 8/1994 | WIPO . |
| WO 94-24931 | 11/1994 | WIPO . |
| WO 95/05771 | 3/1995 | WIPO . |
| WO 95-10322 | 4/1995 | WIPO . |
| WO 96/37146 | 11/1996 | WIPO . |

OTHER PUBLICATIONS

Weston et al, "A Prototype Coronary Electrode . . . Recording", American Journal of Cardiology, vol. 70, Dec. 1, 1992.

Primary Examiner—Lee Cohen
Attorney, Agent, or Firm—Heller Ehram White & McAuliffe

[57] ABSTRACT

An over-the-wire electrophysiology catheter which has an emitting electrode on the distal tip electrically connected to a source of high frequency electrical energy. The intravascular device is configured to be advanced through a patient's cardiac veins or coronary arteries and preferably is also provided with sensing electrodes for detecting electrical activity of the patient's heart from within a blood vessel of the heart. The device forms large lesions in tissue adjacent to the blood vessel in which the device is located without significantly damaging the blood vessel to effectively terminate signals causing arrhythmia.

4 Claims, 6 Drawing Sheets

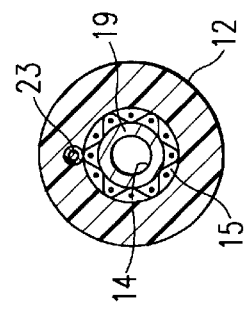
FIG. 1
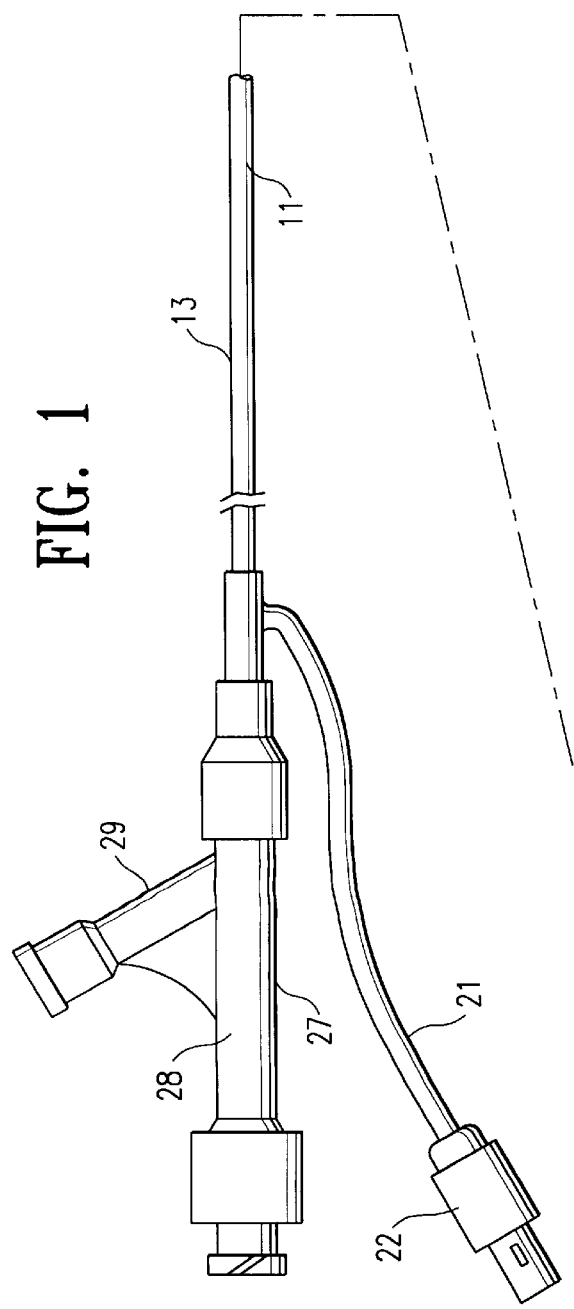
FIG. 2
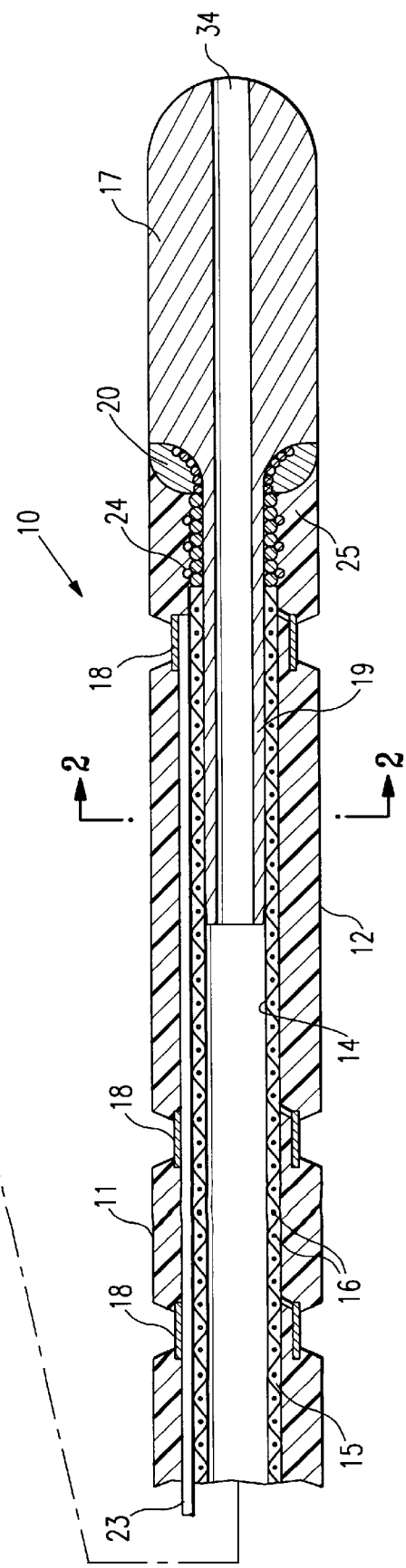

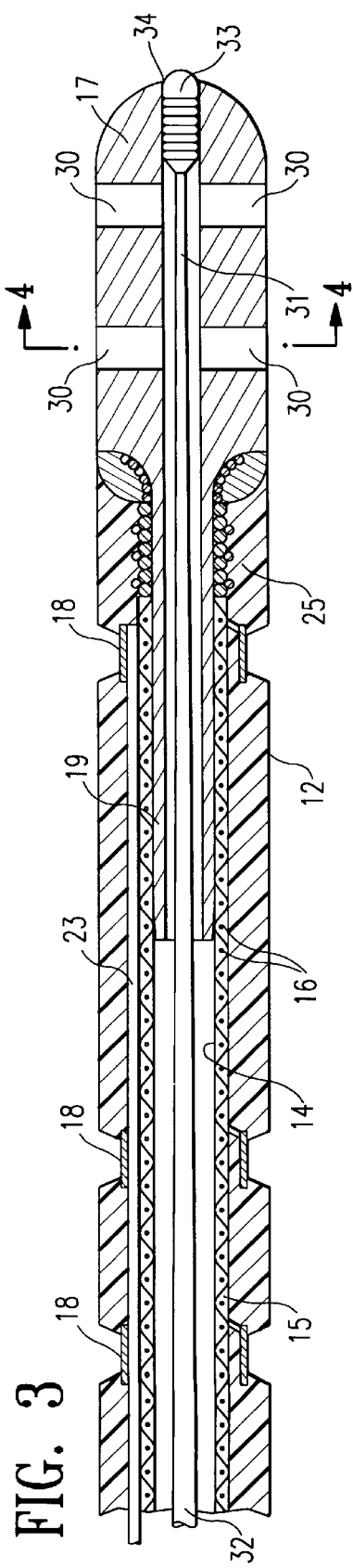
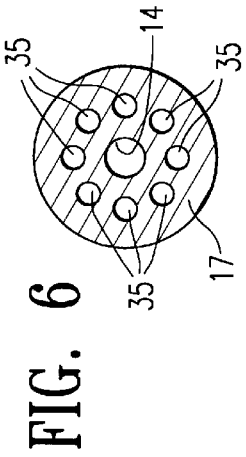
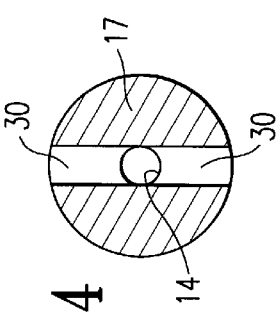
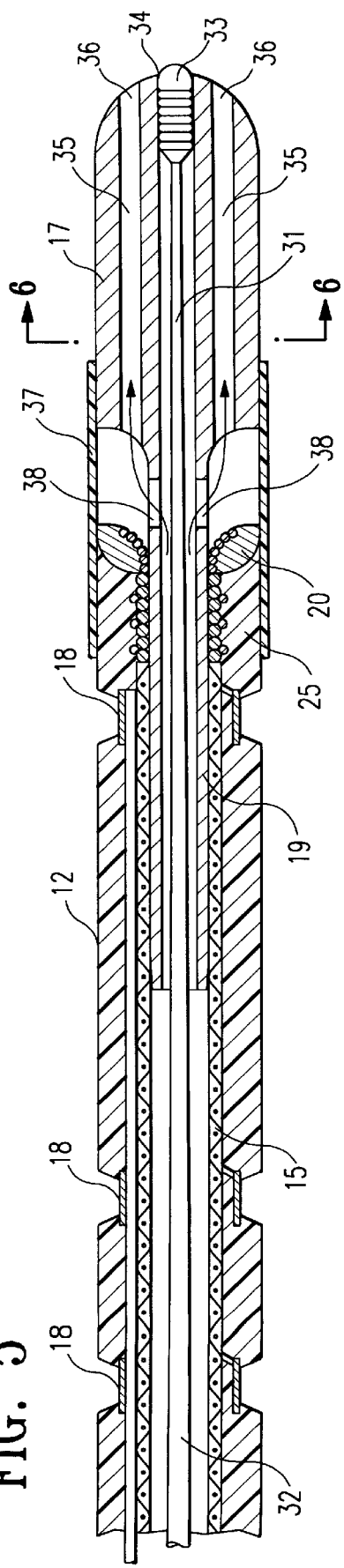

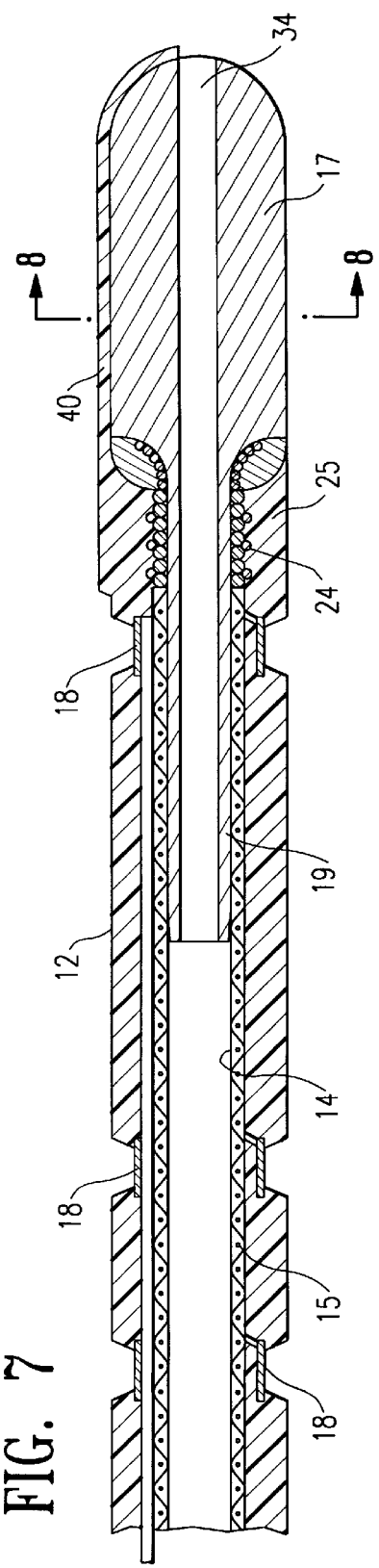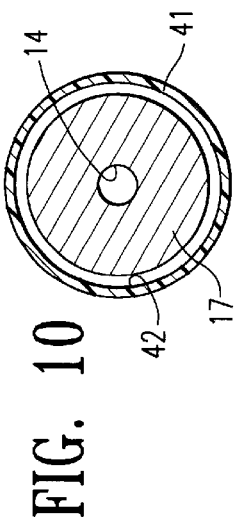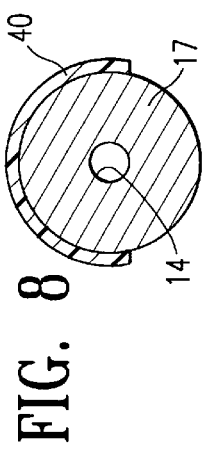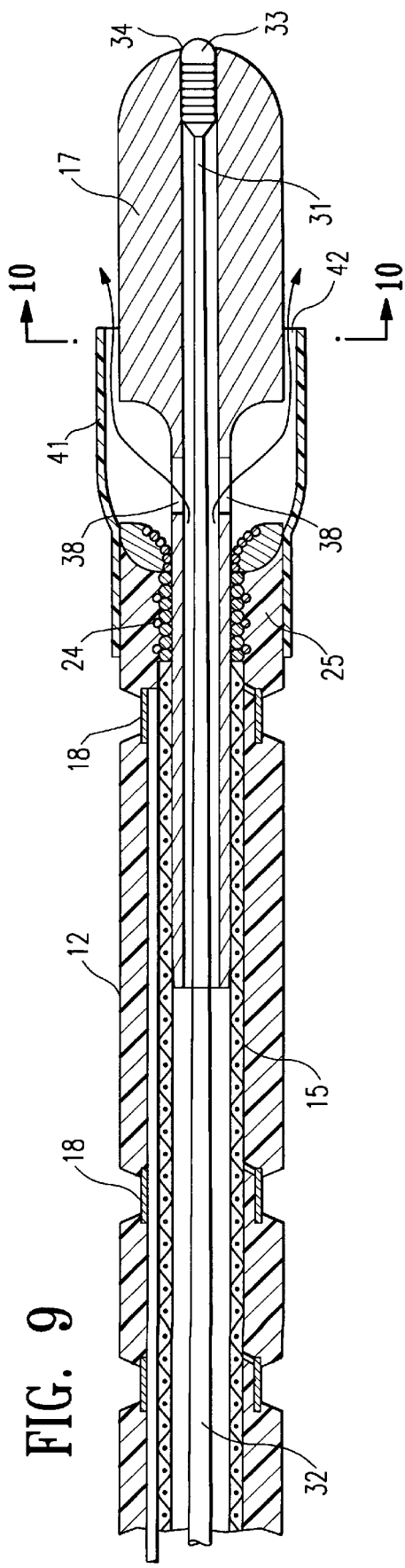

METHOD OF TREATING USING AN OVER-THE-WIRE EP CATHETER

This is a continuation of application Ser. No. 08/473,525, which was filed on Jun. 7, 1995, now abandoned, which is a divisional of Ser. No. 08/447,351, filed May 23, 1995, now U.S. Pat. No. 5,782,760.

BACKGROUND OF THE INVENTION

This invention generally relates to a system for detecting electrical activity or signals within a patient's heart and particularly for determining the source of signals causing arrhythmia from within a blood vessel of the patient's heart.

Prior methods for treating a patient's arrhythmia include the use of antiarrhythmic drugs such as sodium and calcium channel blockers or drugs which reduce the Beta-adrenergic activity. Other prior methods include surgically sectioning the origin of the signals causing the arrhythmia or the conducting pathway for such signals. More frequently, however, to terminate the arrhythmia the heart tissue which causes the arrhythmia is destroyed by heat, e.g. applying a laser beam or high frequency electrical energy, e.g. RF or microwave, to a desired location on the patient's endocardium In the latter instance, the location of the tissue site causing or involved with the arrhythmia must be accurately known in order to be able to contact the desired location with a tissue destroying device. A major problem of ablating the site of the origin of the signals or a conductive pathway is to accurately determine the location of the site so that an excessive amount of good tissue is not damaged or destroyed along with the arrhythmogenic site, while at the same time ensuring that the arrhythmia does not return. For example, the average arrhythmogenic site consists of an area of about 1.4 $cm^2$ of endocardial tissue, whereas a re-entrant site might be much larger. RF ablation techniques produce lesions about 0.5 $cm^2$ in area, so several lesions may be necessary to completely ablate an area of interest. If the arrhythmogenic or re-entrant site is not accurately mapped, much good tissue surrounding the site will be unnecessarily damaged or destroyed.

A variety of prior methods have been used to detect electrical activity within a patient's heart to facilitate the mapping of electrical activity causing the arrhythmia. A number of these prior methods are disclosed in U.S. Patents which use elongated intravascular signal sensing devices with one or more electrodes on a distal portion of the device which are advanced through the patient's vasculature until the distal portions of the sensing devices are disposed within one or more of the patient's heart chambers with one or more electrodes in contact with the endocardial lining. While this procedure is widely used, it does not always allow the site of arrhythmogenic signals to be accurately determined.

In copending application Ser. No. 08/188,619, filed Jan. 27, 1994, now U.S. Pat. No. 5,509,411, reference is made to intravascular devices which are advanced through a patient's coronary arteries or cardiac veins to desired locations in the patient's epicardium where electrical activity is detected by means of electrodes on the distal ends of the devices to locate arrhythmogenic sites or conductive pathways causing or involved with arrhythmia. In copending application Ser. No. 08/207,918, filed Mar. 8, 1994, now abandoned, an intravascular device is described which uses RF energy to occlude a blood vessel in order to destroy tissue distal to the catheter by creating ischemic conditions therein.

What has been needed is a method and system for accurately detecting the source of signals which cause the arrhythmia and to create an lesion which effectively terminates the arrhythmia without detrimentally effecting tissue not involved with the arrhythmia.

SUMMARY OF THE INVENTION

This invention is directed to an elongated intravascular device for creating a lesion in tissue adjacent a patient's blood vessel from within a patient's blood vessel. The device preferably has means for detecting electrical activity in adjacent tissue from within the blood vessel to facilitate accurate placement of the device within the blood vessel to ensure creating an effective lesion. The device is particularly suitable for creating a lesion in a patient's heart which terminates the electrical activity causing an arrhythmia.

The intravascular device of the invention comprises an elongated shaft with proximal and distal ends, a port in the distal end and a guidewire lumen extending through at least the distal section of the shaft to the guidewire port in the distal section. The distal section of the shaft is configured so as to be advanceable through the desired blood vessel or other desired body lumen, such as the patient's coronary arteries or cardiac veins. The device may also be used in blood vessels or other body lumens in other parts of the patient's body.

In accordance with the invention, distal shaft section is provided with at least one emitting electrode which is electrically connected by means of a conductor which extends through the shaft to a high frequency electrical energy source exterior to the patient. The emitting electrode on the distal shaft section preferably forms the distal tip of the elongated shaft and has an inner lumen extending to the port in the distal end which is a continuation of the lumen extending within the shaft. This allows the intravascular device to be advanced over a guidewire to the desired location within a body lumen where the ablation is to occur.

To form an effective lesion in the tissue adjacent to the body lumen without causing unnecessary tissue damage, the temperature of the emitting electrode should be controlled during emission between about 70° C. and 100° C. and preferably about 75° C.–85° C.

To effectively cool the electrode, it is preferably provided with one or more fluid directing passageways which extend radially or longitudinally to facilitate passage of cooling fluid when the emitting electrode is in operation. Alternatively, the emitting electrode may be provided with a sheath on the exterior thereof which directs cooling fluid along the outer surface to control surface temperatures. The emitting electrode may be provided with a proximal tubular extension which is secured by a suitable adhesive within the inner lumen extending within the shaft.

In one presently preferred embodiment, a plurality of sensing electrodes are also provided on the distal shaft section proximal to the emitting electrode so that electrical activity can be detected in tissue adjacent to the body lumen to ensure accurate placement of the emitting electrode within the body lumen and effective lesion formation. The sensing electrodes may be electrically configured for monopolar or multipolar operative modes. Up to 15 or more sensing electrodes may be provided along the distal shaft section. The sensing electrodes may have constant or variable electrode spacings and they may be arranged in a first array of sensing electrodes with a compact spacing and a second array of sensing electrodes with a much greater spacing than that in the first array. In this latter embodiment, the second array of sensing electrodes may be used to detect the general location of electrical activity, such as an arrhythmogenic site or pathway, and then the first array may be utilized to more accurately pinpoint the area of interest based upon the general location detected by the first array of sensing electrode means. The interelectrode spacing in the second array of electrodes should be between about 0.25 and about 2 mm, preferably between about 0.5 and about 1.5 mm, and the interelectrode spacing between the electrodes in the first array may be about 1 to about 10 mm. When a bipolar or multipolar mode of sensing is to be used, the spacing between a pair of bipolar electrodes may be much less than the spacing between pairs of bipolar electrodes.

The shaft of the intravascular device is preferably formed of a plurality of individually insulated electrical conductors braided or wound into an elongated tubular member with the inner lumen extending therein. However, not all of the braided strands which make up the tubular member need be electrical conductors. Some may be high strength fibers such as nylon, Kevlar® and the like. The insulation on individual electrical conductors is exposed adjacent to each of the electrodes to facilitate an electrical connection with the electrode and the electrode may be secured to the exposed conductor by means of a suitable solder or brazing material. The sensing electrodes may be secured by their inner periphery to the underlying tubular member formed of electrical conductors by a suitable adhesive to further ensure maintenance of electrical contact between the electrodes and the exposed conductors.

The sensing electrodes may be circular bands about 0.25 to about 1 mm in width (the longitudinal dimension when on the device) and are preferably made from conducting material such as gold which is biocompatible with the body fluids.

A plastic jacket, preferably a lubricous polymer such as a thermoplastic fluoropolymer, Pebax or a polyethylene may be provided on the exterior of the shaft with a slight overlap of the jacket over the edges of the individual electrodes to prevent exposure of a sharp metallic edge which can cause damage when the elongated device is advanced through blood vessels. The entire exterior of an electrode need not be exposed. For example, the plastic jacket may be disposed about the distal shaft section on which the electrodes are mounted and holes may be made in the jacket to expose small portions of the underlying electrodes. The proximal ends of the electrical conductors connected to the electrodes are electrically connected to one or more multi-pin connectors on the proximal end of the shaft which may be configured to be connected to a receiving member in electrical communication with a video unit which can display representations of the electrical activity sensed.

When using the intravascular device of the invention, a guiding catheter is first introduced into the patient's vasculature and advanced therein until the distal tip of the guiding catheter is seated within the ostium of the coronary sinus or the ostium of a coronary artery. A guidewire is then advanced through the guiding catheter out the distal end thereof and then directed to a desired venous or arterial branch. The intravascular device of the invention is advanced over the guidewire to the desired location where the lesion is to be formed. The sensing electrodes on the distal section of the intravascular device are used to detect the electrical activity causing or involved with the arrhythmia. Once located, the position of the intravascular device can be adjusted to the extent necessary to place the emitting electrode on the distal tip of the device within the vessel as close as possible to the tissue causing or involved with the arrhythmia so, when the lesion is formed by emitting high frequency electrical energy, the tissue in question is within the lesion.

With the device of the invention, the arrhythmogenic site is accurately detected and the lesion formed is large enough to encompass the site with little damage to tissue not involved with the arrhythmia so as to effectively and permanently terminate the arrhythmia. These and other advantages of the invention will become more apparent from the following detailed description of the invention and the accompanying exemplary drawings.

BRIEF DESCRIPTION OF THE DRAWINGS

FIG. 1 is an elevational view of an intravascular device having features of the invention wherein an emitting electrode is provided on the distal end of the device for the delivery of high frequency electrical energy.

FIG. 2 is a transverse cross-sectional view of a distal portion of the intravascular device shown in FIG. 1 taken along the lines 2—2.

FIG. 3 is a longitudinal cross-sectional view of a distal portion of an alternative embodiment of the invention wherein a plurality of radially extending passageways are provided in the emitting electrode to allow for the passage of cooling fluid.

FIG. 4 is a transverse cross-sectional view of the embodiment shown in FIG. 3 taken along the lines 4—4.

FIG. 5 is a longitudinal cross-sectional view of a distal portion of another alternative embodiment of the invention wherein a plurality of longitudinally extending passageways are provided in the emitting electrode to allow for the passage of cooling fluid.

FIG. 6 is a transverse cross-sectional view of the embodiment shown in FIG. 5 taken along the lines 6—6.

FIG. 7 is an elevational view, partially in section, of another alternative embodiment of the invention wherein a portion of the emitting electrode is provided with an insulating sheath.

FIG. 8 is a transverse cross-sectional view of the catheter shown in FIG. 7 taken along the lines 8—8.

FIG. 9 is an elevational view, partially in section, of another alternative embodiment of the invention wherein a sheath is positioned on the exterior of the proximal end of the emitting electrode to direct cooling fluid onto the outside of the electrode.

FIG. 10 is a transverse cross-sectional view of the catheter shown in FIG. 9 taken along the lines 10—10.

DETAILED DESCRIPTION OF THE INVENTION

Figure 12:
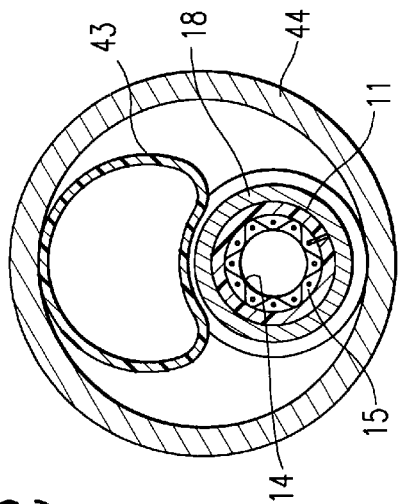
FIG. 12 is a transverse cross-sectional view of the catheter shown in FIG. 11 taken along the lines 12—12.

Reference is made to FIGS. 1–2 which schematically illustrate an embodiment of the invention wherein the elongated intravascular device 10 includes shaft 11 with a distal section 12 and a proximal section 13 and an inner lumen 14 extending within the shaft. The shaft 11 has a braided tubular member 15 formed of a plurality of electrical conductors 16. All the strands forming the tubular member 15 need not be conductors 16, some may be formed of polymer materials such as nylon or Kevlar®. The distal section 12 of the shaft 11 is provided with an emitting electrode 17 at the distal tip and a plurality of sensing electrodes 18 located proximal to the emitting electrode.

The emitting electrode 17 has a proximal tubular extension 19 which extends within the inner lumen 14 and is secured by suitable adhesive to the interior surface of the braided tubular member 15. One or more individual insulated electrical conductors 16 are electrically connected by solder 20 to the emitting electrode 17. Individual insulated electrical conductors 16 are also electrically connected to the sensing electrodes 18 by solder (not shown). The conductors 16 extend to the proximal end of the shaft 11 where they are bundled and formed into cable 21 leading to multiple pin electrical connector 22 where each electrical conductor is connected to a separate pin (not shown). The proximal extremity of the conductor or conductors electrically connected to the emitting electrode 17 are electrically connected through the pins to a source of high frequency electrical energy (RF or microwave) and the proximal extremities of the conductors electrically connected to sensing electrodes 18 are connected through the pins to a display system (not shown) where representations are presented on the signal received by the sensing electrodes.

Preferably a safety wire 23 extends within the wall of the shaft 11 and is secured by its distal end to the emitting electrode 17 to prevent its loss within the patient. The distal extremity 24 of the safety wire 23 is coiled within the shaft wall proximal to the emitting electrode 17 and is bonded by suitable adhesive 25 to the proximal extension 19. The proximal end of the safety wire may be secured to the a band (not shown) in the shaft 11 spaced proximal to the emitting electrode 17.

A conventional adapter 27, which is secured to the proximal end of the shaft 11, has a central arm 28 for entry of a guidewire into the inner lumen 14 and a side arm 29 also in fluid communication with the inner lumen 14 for delivery of flushing or cooling fluid to the emitting electrode 17 on the distal section of the shaft. An O-ring may be provided in the proximal hub of the central arm 28 to prevent the escape of fluid.

The embodiment shown in FIGS. 3 an 4 is essentially the same as the embodiment shown in FIGS. 1 and 2 (and is similarly numbered) except that a plurality of radially extending passageways 30 extend between the inner lumen 14 and the exterior of the electrode 17. The guidewire 31, having a core 32 and a coil 33 on the distal extremity of the core, is slidably disposed within the inner lumen 14 and the coil on the distal end of the guidewire extends beyond the passageways 30 and to a significant extent occludes the inner lumen 14 and reduces considerably the passage of fluid through the port 34 in the distal tip of the emitting electrode 17. Fluid flowing through the inner lumen 14 will then be forced to flow through the radial passages 30 thereby cooling the emitting electrode 17.

Another embodiment is shown in FIGS. 5 and 6 where the emitting electrode 17 has longitudinally disposed passageways 35 for directing cooling fluid from the inner lumen 14 through the electrode and out the ports 36 in the distal tip of the electrode. A tubular sheath 37 formed of a high strength polymer material, such as polyimide, extends between the body of adhesive 25 securing the coiled distal extremity of the safety wire 24 to the tubular extension 19 of the emitting electrode 17 to the proximal end of the electrode to direct fluid which passes from the inner lumen 14 through the ports 38 in the tubular extension 19 to the passageways 35 as indicated by the arrows shown in FIG. 5. The intravascular device shown is otherwise essentially the same as the prior devices and is similarly numbered. A guidewire 31 may be used to occlude inner lumen 14 as in the prior embodiment to ensure an adequate flow of cooling fluid through passageways 35 to maintain the temperature of the emitting electrode 17 at a desired level.

FIGS. 7 and 8 illustrate yet another embodiment of the invention wherein an arcuate insulating sheath 40 is secured about an exterior portion of the emitting electrode 17 to ensure a more focused emission of high frequency electrical energy from a smaller exposed portion of the electrode toward the tissue to be treated to control the size of the lesion formed. This device is for the most part the same as the previously discussed embodiments, except for insulation sheath 40, and is therefore similarly numbered.

Another embodiment is depicted in FIGS. 9 and 10 wherein a fluid control sheath 41 which is secured by its proximal extremity to the adhesive 25 and extends over the exterior of the emitting electrode 17. The inner diameter of the distal end of the sheath 41 is slightly larger than the outer diameter of the electrode 17 to provide an annular gap 42 therebetween which directs cooling fluid along the exterior surface of the electrode as indicated by the arrows. The cooling fluid passes from the inner lumen 14 through the ports 38 in the tubular extension 19 and through the annular gap 42. In this embodiment a guidewire 31 is disposed within the inner lumen 14 with the coil 33 at least partially occluding the distal portion of the inner lumen so that an adequate flow of cooling fluid passes along the exterior of the electrode 17 to ensure sufficient cooling thereof.

Figure 11:
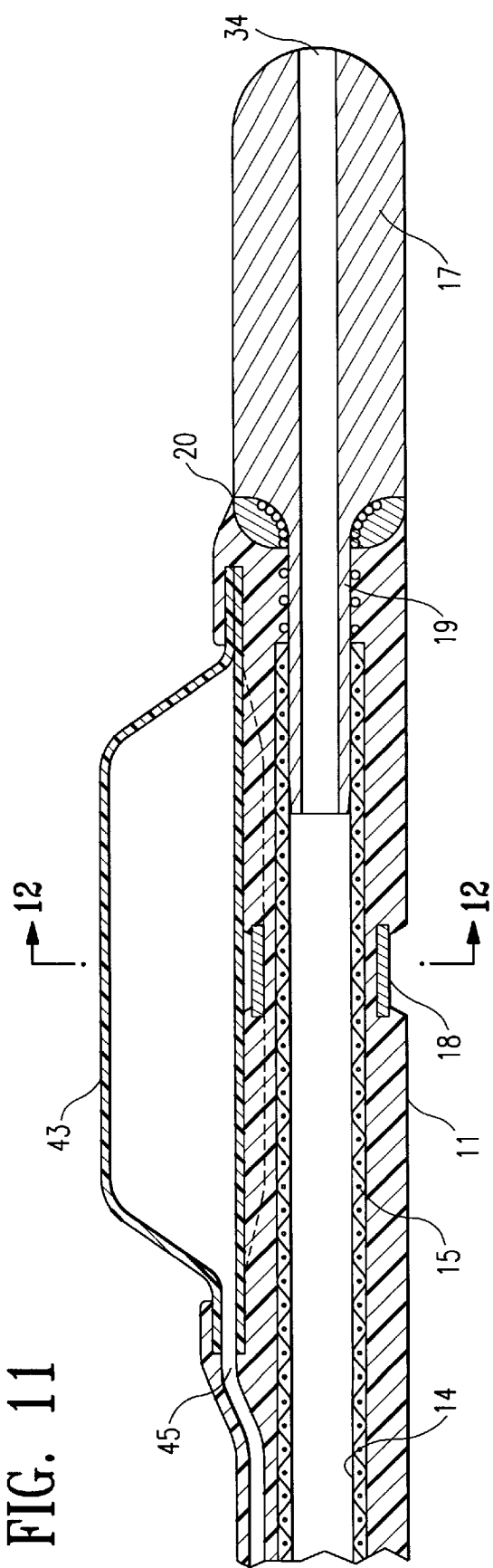
FIG. 11 is an elevational view, partially in section, of another alternative embodiment of the invention wherein an expandable balloon is provided on one side of the distal section of the device so when it is inflated, the emitting electrode will be urged against the interior of the body lumen.

In larger blood vessels, it frequently is difficult to maintain contact between the emitting electrode 17 and the blood vessel wall. To overcome this problem, it is desireable to provide an expandable positioning member, such as an inflatable balloon 43, which when inflated ensures contact between a desired portion of the blood vessel wall 44 and the emitting electrode 17 as shown in FIGS. 11 and 12. An inflation lumen 45 extends through the shaft 11 from its proximal end to a location within the interior of the balloon 43. To accommodate for the extra lumen a three arm adapter (not shown) is secured to the proximal end of the shaft. While only one sensing electrode 18 is shown in the drawings, a plurality of sensing electrodes may be provided proximal to the balloon 43. The maximum transverse dimension of the balloon 43 as measured from the opposite side of the shaft 11 may range from about 0.5 to about 5 mm, preferably about 1.5 to about 4 mm.

Figure 13:
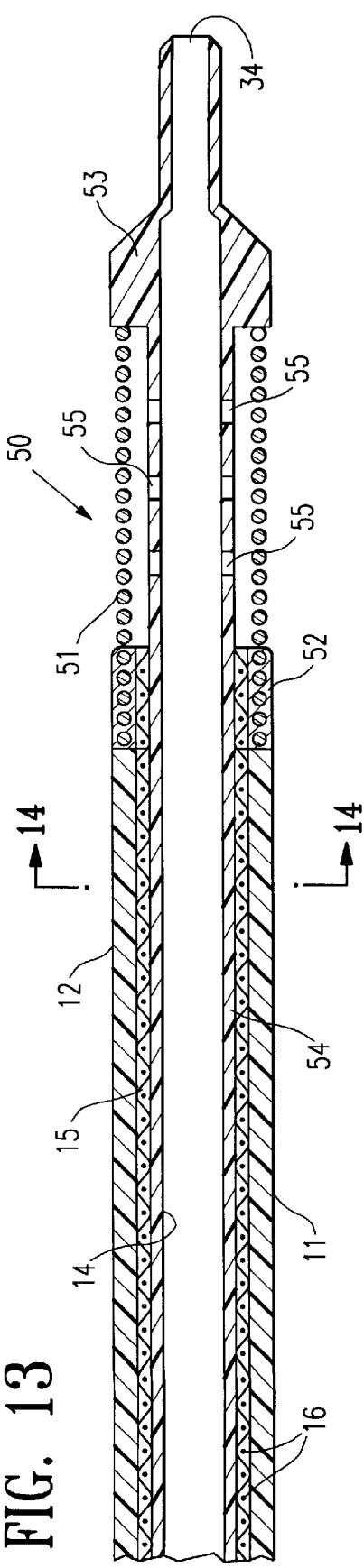
FIG. 13 is a longitudinal cross-sectional view of another alternative embodiment of the invention wherein the distal section of the device is provided with an emitting electrode formed of a coiled wire.
Figure 14:
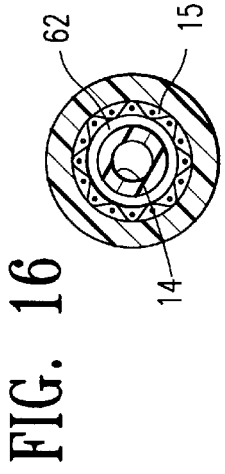
FIG. 14 is a transverse cross-sectional view of the catheter shown in FIG. 13 taken along the lines 14—14.

FIGS. 13 and 14 represent another embodiment where the emitting electrode 50 is a helical coil on the distal end of the shaft 11. The proximal end of the coil 51 is secured by solder 52 to the distal end of the shaft 11 shown in FIG. 13 to facilitate an electrical connection with the conductors 16 in the shaft 11 and the distal end of the coil is secured by adhesive to the enlarged distal end 53 of the lining 54. Perfusion holes 55 are provided in lining 54 to allow fluid passing through inner lumen 14 to contact and thus cool the coil 51.

Figure 16:
FIG. 16 is a transverse cross-section of the catheter shown in FIG. 15 taken along the lines 16—16.
Figure 15:
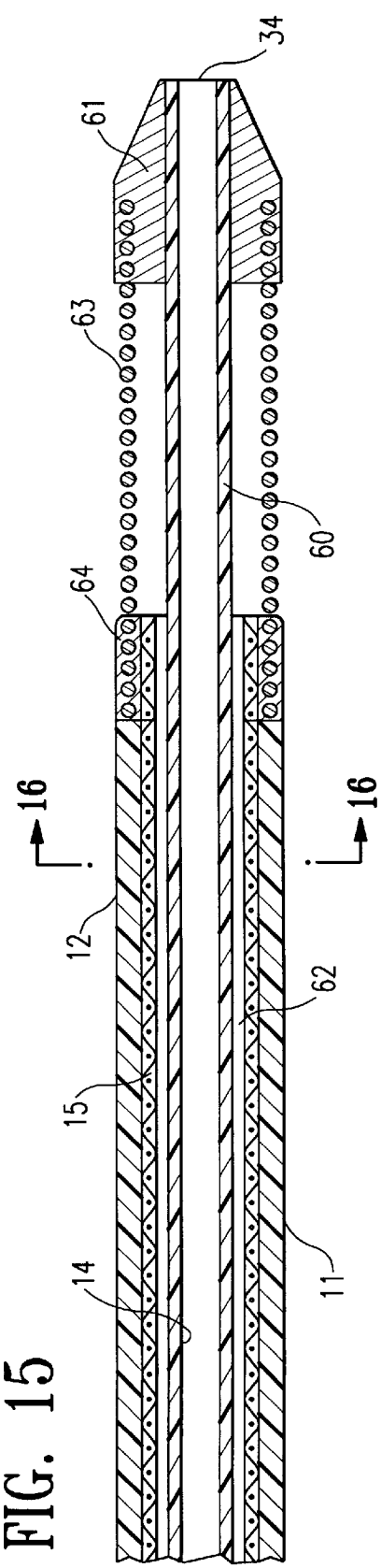
FIG. 15 is a longitudinal cross-sectional view of an embodiment similar to that shown in FIGS. 13 and 14 but with separate guidewire and fluid lumens.

In the embodiment shown in FIGS. 15 and 16 the inner lumen 14 is disposed within the inner tubular member 60 which extends to the distal tip 61. Annular lumen 62 extends between the interior surface of braided tubular member 15 and the exterior surface of inner tubular member 60. Electrode coil 63 is secured by its proximal end to the shaft 11 by solder 64 and is electrically connected to a conductor of the braided tubular member 15. The distal end of the coil 63 is secured to the distal tip 61 by a suitable adhesive or by fusing the distal tip about the distal end of the coil. In this embodiment the delivery of cooling fluid through the annular lumen 62 is independent of a guidewire (not shown) in lumen 14.

Figure 17:
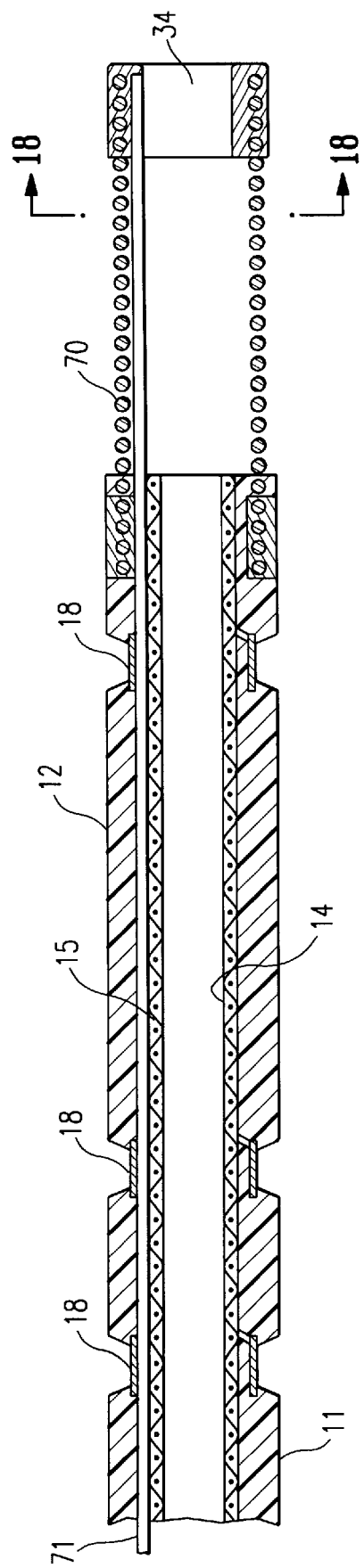
FIG. 17 is a longitudinal cross-sectional view of the distal section of another embodiment of the invention.
Figure 18:
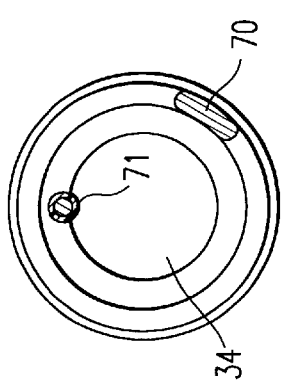
FIG. 18 is a transverse cross-sectional view of the embodiment shown in FIG. 17 taken along the lines 18—18.

FIGS. 17 and 18 illustrate the distal portion of yet another embodiment of the invention where an emitting coil electrode 70 is secured to the distal tip of shaft 11 by means of adhesive or solder. A safety wire 71, which extends through the shaft 11 as in the previous embodiments, is soldered to the distal tip of the emitting coil electrode 70. Sensing electrodes 18 are provided on shaft 11 proximal to the emitting electrode coil 70 as in the previous embodiments. The details of shaft 11 are the same as shown in the prior embodiments.

The overall length of the intravascular devices of the invention may range from about 80 to about 300 cm, typically about 120 to about 175 cm for delivery through the femoral artery or vein and about 80 to about 120 cm for delivery through the brachiocephalic artery or internal jugular vein. Because the intravascular device is to be advanced over a guidewire, the guidewire must be longer than the catheter by about 20 to about 60 cm. The outer diameter of the shaft of the intravascular device should be less than about 0.065 inch (1.65 mm) and preferably about 0.035–0.06 inch (0.89–1.5 mm). The inner lumen 14 has an inner diameter of about 0.01 to about 0.04 inch (0.25–1 mm) to facilitate the reception and advancement of a guidewire therethrough, which is typically about 0.010 to about 0.018 inch (0.25–0.46 mm) in outer diameter. The diameter of the inner lumen through the emitting electrode may be much smaller than the diameter of the inner lumen in the more proximal portions of the shaft 11. The distal section 12 of the shaft is about 3 to about 20 cm in length. An intermediate section having an intermediate stiffness may be provided between the proximal section 13 and the distal section 12 with a length of about 5 to about 40 cm in length, typically about 20 cm in length. The radial passageways 30 are typically about 0.02 inch (0.5 mm) in diameter and the longitudinal passageways 35 are typically about 0.01 inch (0.25 mm). The emitting electrode is generally longer than about 2 mm. For solid electrodes the length is generally less than about 10 mm, but for an emitting electrode in the form of helical coil the length may be about 2 to about 30 mm, preferably about 2 to about 20 mm.

To the extent not previously described, the materials of construction of the intravascular device of the invention may be formed of conventional materials. The electrical conductors 16 may be electrical grade copper wire about 0.003 inch (0.08 mm) in diameter which are provided with a thin insulated jacket or coating of polyimide or other suitable insulator. The outer jacket may be a thermoplastic polyurethane such as PBAX which is available from Eif Atochem Polymers of Philadelphia, Pa. The jacket of the proximal section is preferably Pebax 1147, the jacket of the intermediate section is Pebax 6333 and the jacket of the distal section is Pebax 4033. The sensing and emitting electrodes are preferably formed of an alloy of platinum and iridium, e.g. 90% Pt and 10% Ir (wt. %) or of Gold (100%). The safety wire 23 may be a stainless steel wire about 0.003 inch (0.08 mm) in diameter with a polyimide coating. The preferred solder used to join the electrical conductors to the various electrodes is 95% Sn-5% Ag or 80% Au-20% Sn.

One presently preferred method of using the elongated intravascular device includes first advancing a guiding catheter through the patient's vascular system until the distal tip of the guiding catheter is seated within the coronary sinus ostium or the ostium of one of the coronary arteries. The guiding catheter is torqued by its proximal extremity which extends out of the patient to guide the distal tip into the selected ostium. Once the distal end of the guiding catheter is seated, the intravascular device of the invention with a guidewire slidably disposed within the inner lumen thereof are advanced through the guiding catheter and out the distal end thereof. The guidewire is first advanced into the target vein or artery and the intravascular device of the invention is advanced over the guidewire into the target blood vessel. The sensing electrodes 18 on the intravascular device of the invention are used to detect electrical activity which allows the physician or operator to determine the location of the arrhythmogenic focus. When the focus is located, the intravascular device is moved within the blood vessel, as required, to position the emitting electrode 17 as close as possible to the focus. High frequency electrical energy, preferably in the RF range, is directed through the electrical conductors 16 connected to the emitting electrode 17 to form the desired lesion which encompasses the arrhythmogenic focus. Energy levels of about 5 Watts to about 100 Watts, preferably about 30 Watts to about 70 Watts are suitable to terminate most arrhythmias. Typical lesions formed are about 3 mm to about 20 mm in diameter and about 3 mm to about 20 mm in length. In some instances, where the site of the arrhythmic activity is detected by other means, an intravascular device may be utilized which does not have sensing electrodes. For example, the guidewire utilized to advance the intravascular device of the invention into the desired blood vessel may be provided with sensing electrodes for detecting the electrical activity of interest. A suitable device is described in copending application Ser. No. 08/188,619, filed Jan. 27, 1994, which is incorporated herein by reference.

While there are several means described herein to cool the emitting electrode, a wide variety of means can be used to control the temperature of the emitting electrode. For example, the electrical energy to the emitting electrode can be controlled so as to maintain the temperature thereof. A thermistor or other temperature sensing device can be employed to monitor the electrode temperature and the temperature sensed is used to control in a conventional feedback arrangement the electrical power delivery.

Although individual features of one embodiment of the invention may be described herein and shown in one or more of the drawings and not in others, those skilled in the art will recognize that individual features of one embodiment of the invention can be combined with any or all the features of another embodiment of the invention. Various modifications and improvements may be made to the invention without departing from the scope thereof.

What is claimed is:

1. A method of treating a patient's heart experiencing arrhythmia comprising:

a) providing an intravascular catheter having an elongated shaft having proximal and distal ends, a port in the distal end, an inner lumen extending within the shaft to the port in the distal end, a distal tip emitting electrode on the elongated shaft, with at least one lumen extending therethrough in fluid communication with the inner lumen of the shaft, and with a port in a distal end of the emitting electrode configured to slidably receive a guidewire therethrough, at least one electrical conductor in electrical contact with and extending proximally from the emitting electrode and configured to be electrically connected to a high frequency electrical energy source, and a plurality of electrodes on a distal portion of the elongated shaft;

b) percutaneously introducing a guidewire into the patient's vasculature, advancing the guidewire into the coronary sinus or coronary artery of the patient's heart and steering the guidewire into a branch blood vessel of the coronary sinus or coronary artery;

c) positioning the guidewire in the port in the distal end of the emitting electrode and advancing the intravascular catheter over the guidewire to a desired location within said branch blood vessel;

d) detecting electrical activity within the patient's heart by said plurality of electrodes on the distal portion of the intravascular catheter to determine the location of a source of arrhythmogenic signals or a conducting pathway therefore;

e) positioning the intravascular catheter within the blood vessel so that the emitting electrode is adjacent to the location; and f) emitting high frequency electrical energy at least from the emitting electrode to form a lesion within the patient's heart encompassing tissue at said source of arrhythmogenic signals, or in the conducting pathway therefore, said tissue being outside of the blood vessel in which the intravascular catheter is located.

2. The method of claim 1 wherein the guidewire has a plurality of electrodes, and the step of detecting the electrical activity includes detecting electrical activity by the electrodes on the guidewire.

3. The method of claim 1 including controlling the temperature of the emitting electode to less than about 100° C.

4. The method of claim 1 including controlling the temperature of the emitting electrode by directing cooling fluid from the inner lumen of the shaft through at least one lumen in the emitting electrode.

* * * * *